(12) United States Patent
Oh

(10) Patent No.: US 9,008,384 B2
(45) Date of Patent: Apr. 14, 2015

(54) METHOD, SERVER, AND USER DEVICE FOR PROVIDING USER'S PERSONAL MEDICINE INFORMATION MANAGEMENT SERVICE BETWEEN THE SERVER AND THE USER DEVICE

(75) Inventor: Zhang-hoon Oh, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 301 days.

(21) Appl. No.: 13/354,667

(22) Filed: Jan. 20, 2012

(65) Prior Publication Data
US 2012/0189177 A1 Jul. 26, 2012

(30) Foreign Application Priority Data
Jan. 20, 2011 (KR) .................. 10-2011-0005991

(51) Int. Cl.
*G06K 9/00* (2006.01)
*G06F 19/00* (2011.01)
*G06K 9/22* (2006.01)
*G06Q 50/22* (2012.01)

(52) U.S. Cl.
CPC ............ *G06F 19/3418* (2013.01); *G06K 9/228* (2013.01); *G06F 19/3456* (2013.01); *G06Q 50/22* (2013.01)

(58) Field of Classification Search
None
See application file for complete search history.

(56) References Cited

U.S. PATENT DOCUMENTS

| | | | |
|---|---|---|---|
| 2003/0204357 A1 | 10/2003 | Hamilton | |
| 2008/0119958 A1* | 5/2008 | Bear et al. | 700/244 |
| 2011/0231202 A1* | 9/2011 | Hanina et al. | 705/2 |
| 2011/0288884 A1* | 11/2011 | Algoo et al. | 705/3 |

FOREIGN PATENT DOCUMENTS

KR 10-2011-0047764 A 5/2011

* cited by examiner

*Primary Examiner* — Atiba O Fitzpatrick
(74) *Attorney, Agent, or Firm* — Sughrue Mion, PLLC

(57) ABSTRACT

A method of managing a personal medicine information management service by a user device and a server includes obtaining a medicine image captured by photographing appearance of a user medicine; transmitting the obtained medicine image to the server as a request for recognition of the user medicine; and receiving medicine quantity information and personal medicine information from the server based on a result of the recognition of the user medicine. The personal medicine information includes an image of the user medicine of which recognition training is performed by the server.

30 Claims, 13 Drawing Sheets

MEDICINE NAME: AAABBBCINE
REMAINING QUANTITY: 2 PILLS
DATE: YYYY.MM.DD PM HH:MM.SS
INGREDIENTS: S, P, Q
EFFECTS: T, U, V, W

<MEDICINE-TAKING HISTORY>
① ~~~~~~~~
② ~~~~~~~~
③ ~~~~~~~~

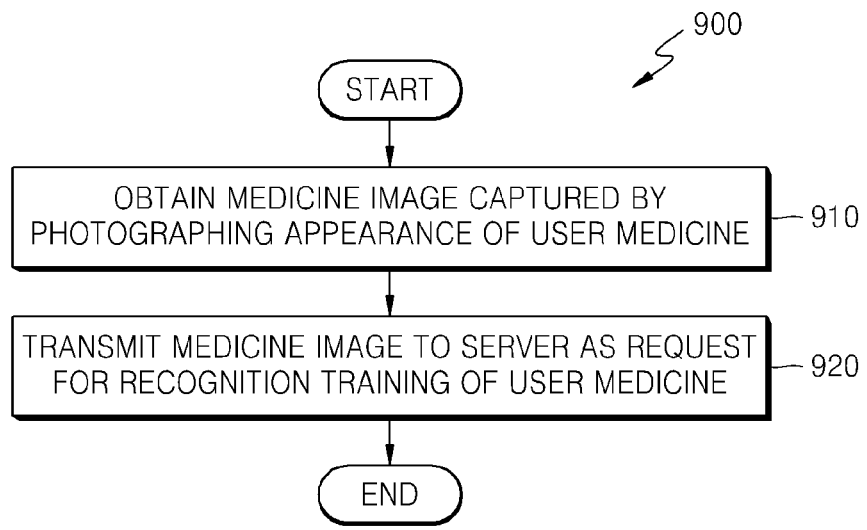
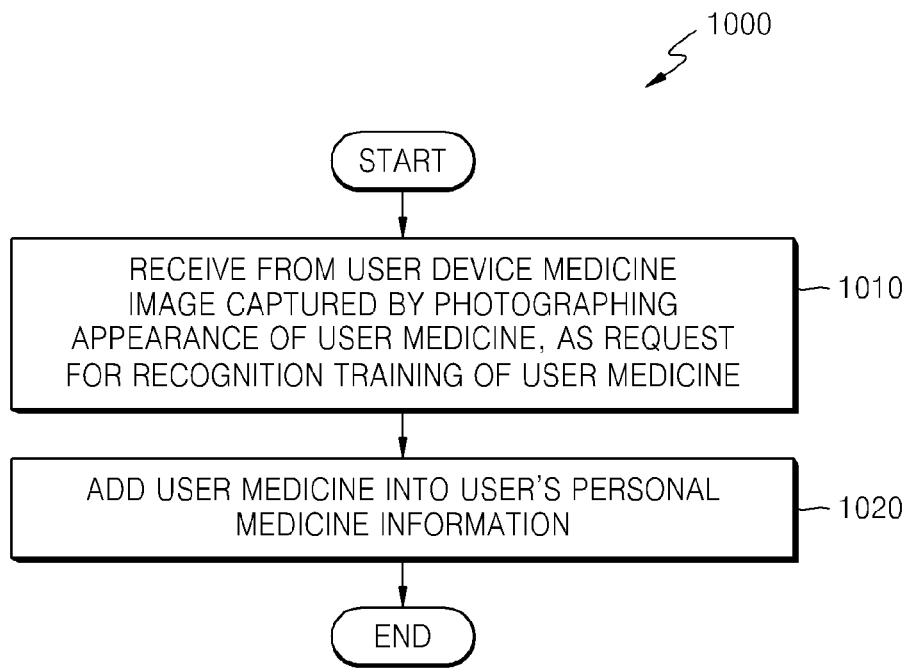

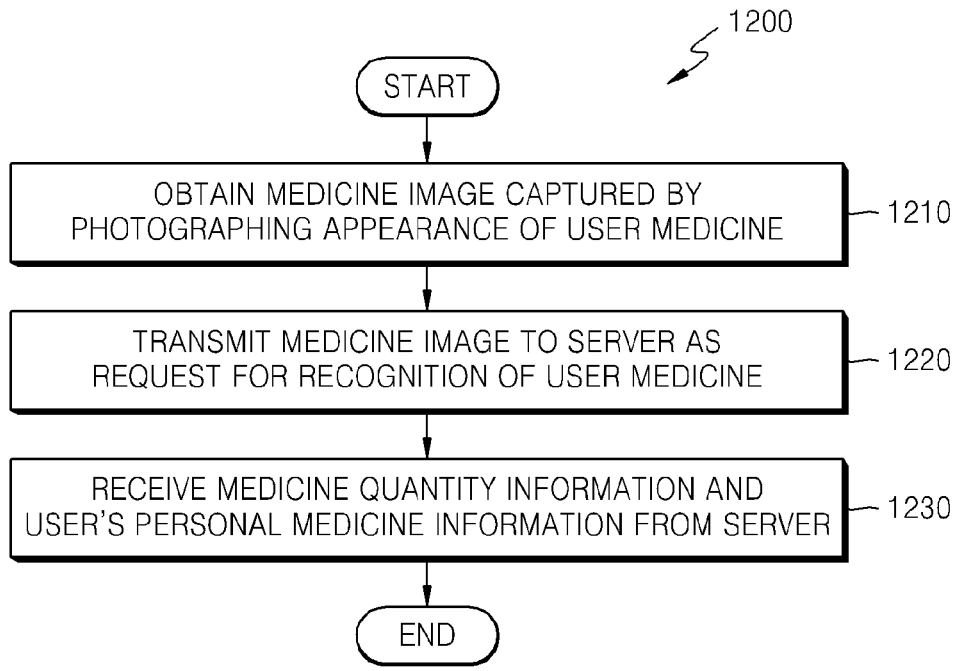
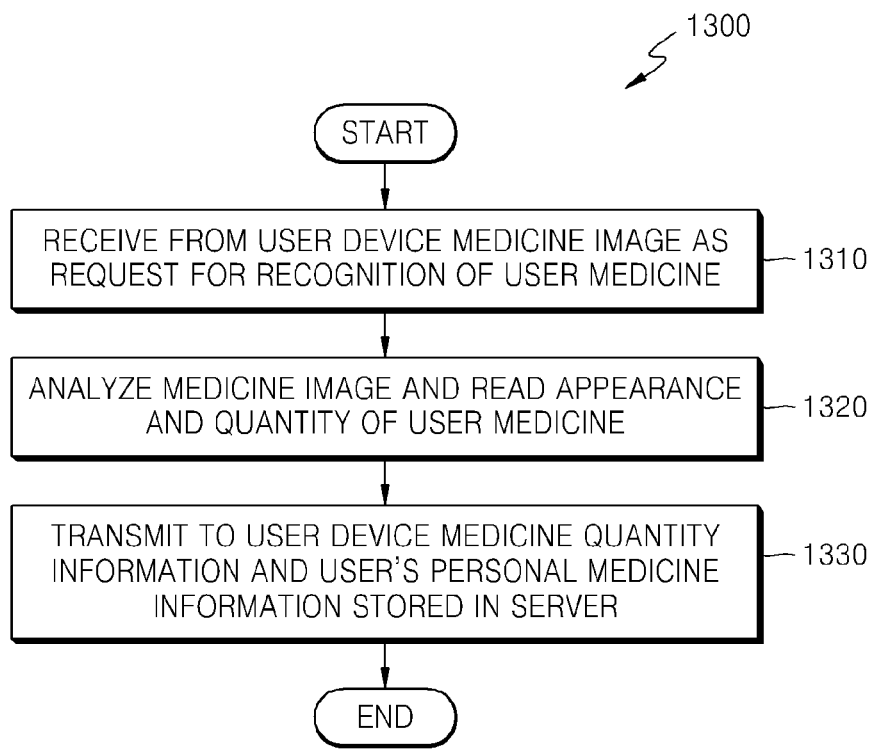

US 9,008,384 B2

METHOD, SERVER, AND USER DEVICE FOR PROVIDING USER'S PERSONAL MEDICINE INFORMATION MANAGEMENT SERVICE BETWEEN THE SERVER AND THE USER DEVICE

CROSS-REFERENCE TO RELATED PATENT APPLICATION

This application claims priority from of Korean Patent Application No. 10-2011-0005991, filed on Jan. 20, 2011 in the Korean Intellectual Property Office, the disclosure of which is incorporated herein by reference in its entirety.

BACKGROUND

1. Field

Methods and apparatuses consistent with the exemplary embodiments relate to a network environment for providing a personal life management service by using a wireless communication technology.

2. Description of the Related Art

A huge number of medicines are developed and sold along with the development of medical technologies. Unlike in the past when the economical development was followed by an increase in life quality, nowadays, many people consider life quality as being more valuable and are interested in living a healthy life style. This has led to increased demands for nonprescription medicines and health supplements. However, drug abuse is harmful and medicines should be taken appropriately.

SUMMARY

Exemplary embodiments relate to a method, a server, and a user device for providing a personal medicine information management service between the server and the user device.

According to an aspect of an exemplary embodiment, there is provided a method of providing a personal medicine information management service by a user device that communicates with a server, the method including: photographing a user medicine to obtain a medicine image of the user medicine; transmitting to the server a request for recognition of the user medicine, the request comprising the obtained medicine image; and receiving medicine quantity information and personal medicine information from the server based on a result of the recognition of the user medicine, wherein the personal medicine information comprises an image of the user medicine of which recognition is performed by the server.

According to another aspect of an exemplary embodiment, there is provided a method of providing a personal medicine information management service by a server, the method including: receiving from a user device a request to recognize of user medicine, the request comprising a medicine image of the user medicine; analyzing the received medicine image to recognize the user medicine and to determine a remaining quantity of the user medicine; and transmitting to the user device medicine quantity information and personal medicine information stored in the server, based on a result of the analyzing, wherein the personal medicine information comprises an image of the user medicine of which recognition is performed by the server.

According to another aspect of an exemplary embodiment, there is provided a method of providing a personal medicine information management service by a user device, the method including: photographing a user medicine to obtain a medicine image of the user medicine; and transmitting to a server a request for recognition of the user medicine, the request comprising the medicine image, wherein, if the recognition of the user medicine is completed by the server, the user medicine is added to personal medicine information by the server.

According to another aspect of an exemplary embodiment, there is provided a method of providing a personal medicine information management service by a server, the method including: receiving from a user device a medicine image of a user medicine, as a request for recognition of the user medicine; and adding the user medicine to personal medicine information based on the received medicine image.

According to another aspect of an exemplary embodiment, there is provided a user device for providing a personal medicine information management service, the user device including: a medicine image obtaining unit that obtains a medicine image of a user medicine; a medicine recognition requesting unit that transmits to a server a request for recognition of the user medicine, the request comprising the obtained medicine image; and a medicine information receiving unit that receives medicine quantity information and personal medicine information from the server based on a result of the recognition of the user medicine, wherein the personal medicine information comprises an image of the user medicine of which recognition is performed by the server.

According another aspect of an exemplary embodiment, there is provided a server for providing a personal medicine information management service, the server including a medicine information storage that stores personal medicine information; a medicine recognition request receiving unit that receives from a user device a request for recognition of user medicine, the request comprising a medicine image of the user medicine; a medicine image reading unit that analyzes the received medicine image to recognize the user medicine and to determine a remaining quantity of the user medicine; and a medicine information transmitting unit that transmits to the user device medicine quantity information and the personal medicine information stored in the server, based on a result of the analyzing, wherein the personal medicine information comprises an image of the user medicine of which recognition is performed by the server.

According to another aspect of an exemplary embodiment, there is provided a user device for providing a personal medicine information management service, the user device including: a medicine image obtaining unit that obtains a medicine image of a user medicine; and a medicine recognition training requesting unit that transmits to a server a request for recognition of the user medicine, the request comprising the medicine image of the user medicine, wherein, if the recognition of the user medicine is completed by the server, the user medicine is added into personal medicine information by the server.

According to another aspect of an exemplary embodiment, there is provided a server for providing a personal medicine information management service, the server including: a medicine information storage that stores personal medicine information; a medicine recognition training request receiving unit that receives from a user device a request for recognition of user medicine, the request comprising a medicine image of the user medicine; and a personal medicine information processing unit that adds the user medicine into the personal medicine information based on recognition of the received medicine image.

According to another aspect of an exemplary embodiment, there is provided a computer-readable recording medium having recorded thereon a computer program for executing the above method of providing a personal medicine information management service by a user device via a server.

According to another aspect of an exemplary embodiment, there is provided a computer-readable recording medium having recorded thereon a computer program for executing the above method of providing a personal medicine information management service by a server.

According to another aspect of an exemplary embodiment, there is provided a computer-readable recording medium having recorded thereon a computer program for executing the above method of providing a personal medicine information management service by a user device to request recognition training of a user medicine.

According to another aspect of an exemplary embodiment, there is provided a computer-readable recording medium having recorded thereon a computer program for executing the above method of providing a personal medicine information management service by a server to perform recognition training of a user medicine.

BRIEF DESCRIPTION OF THE DRAWINGS

The above and other aspects will become more apparent by describing in detail exemplary embodiments, with reference to the attached drawings in which:

FIG. 9 is a flowchart of a method of requesting recognition training of a user medicine by a user device to provide a user's personal medicine information management service, according to an exemplary embodiment;

FIG. 10 is a flowchart of a method of performing recognition training of a user medicine by a server to provide a user's personal medicine information management service, according to an exemplary embodiment;

FIG. 12 is a flowchart of a method of providing a user's personal medicine information management service by a user device via a server, according to an exemplary embodiment;

FIG. 13 a flowchart of a method of providing a user's personal medicine information management service by a server, according to an exemplary embodiment;

DETAILED DESCRIPTION OF THE EXEMPLARY EMBODIMENTS

Users may purchase prescription or non-prescription medicines at drugstores. In most cases, non-prescription medicines directly sold at general drugstores to customers have unique packages for identification purposes and instructions for use purposes outside or inside the packages. However, if the packages or instructions of such medicines are lost, customers may not know how to use the medicines. Also, in the case of prescription medicines, if prescriptions or packages of the medicines are lost, customers may not know how to take or use the prescription medicines.

Accordingly, in a user's personal medicine information management service according to an exemplary embodiment, a server may collect information regarding a personal medicine of the user, identify the personal medicine, and manage a medicine-taking history by checking the remaining quantity of the personal medicine, thereby providing overall information related to the personal medicine to the user. For this, a server for providing a user's personal medicine information management service, according to an exemplary embodiment, may receive and read a medicine image captured by a user device, extract and transmit information regarding a corresponding medicine to the user device, and provide personal medicine information to the user.

Hereinafter, for convenience of explanation, a user's medicine of which an image is captured by a user device and which is not yet recognized by a server is referred to as a 'user medicine', and a user medicine registered in user's personal medicine information by a server is referred to as a 'user's personal medicine'.

A user device 100 and a server 200 for providing a user's personal medicine information management service will now be described with reference to FIGS. 1 and 2.

Figure 1:
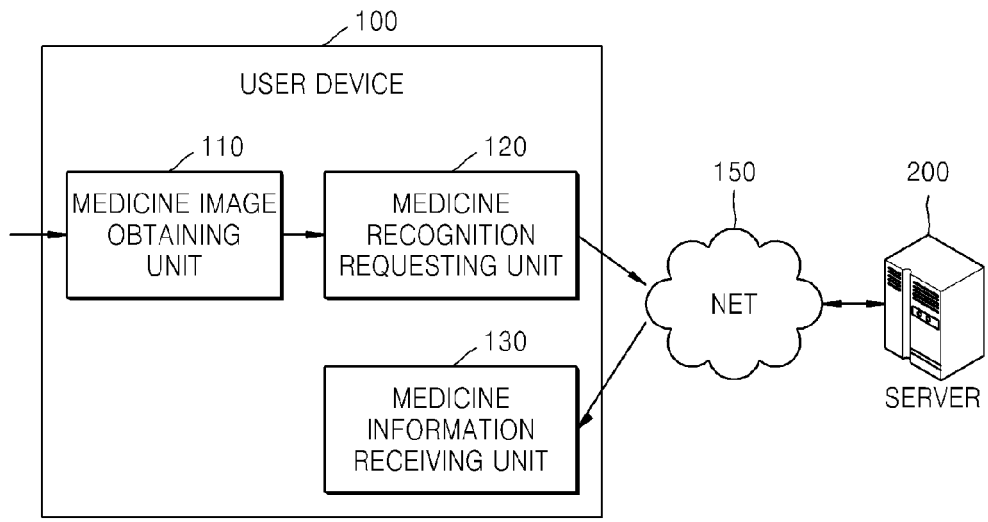
FIG. 1 is a block diagram of a user device for providing a user's personal medicine information management service, according to an exemplary embodiment.

FIG. 1 is a block diagram of the user device 100 for providing a user's personal medicine information management service, according to an exemplary embodiment.

The user device 100 includes a medicine image obtaining unit 110, a medicine recognition requesting unit 120, and a medicine information receiving unit 130. The user device 100 may perform data communication with the server 200 via a wired or wireless communication network 150. Also, the server 200 may be a cloud computing based virtual server.

The medicine image obtaining unit 110 may obtain a medicine image captured by photographing appearance of a user medicine. If an image sensor is included, the medicine image obtaining unit 110 may directly photograph the appearance of the user medicine. If an image sensor is not included, the medicine image obtaining unit 110 may obtain the medicine image captured by an accessible external device, such as a ubiquitous or Bluetooth device.

The obtained medicine image of the user medicine may include images showing the appearance of the user medicine, e.g., an image showing a shape of a medicine itself, and an image showing a shape of a medicine package. Also, the medicine image of the user medicine may include at least one of an image showing non-prescription medicine identification information of the user medicine, and an image showing nonprescription medicine product information of the user medicine, which are readable from the appearance of the user medicine.

The medicine recognition requesting unit 120 may transmit to the server 200 the medicine image obtained by the medicine image obtaining unit 110, as a request for recognition of the user medicine.

The medicine information receiving unit 130 may receive user's personal medicine information and medicine quantity information from the server 200 based on a result of the recognition of the user medicine, in response to the request of the medicine recognition requesting unit 120. The medicine information receiving unit 130 may receive identification information and remaining quantity information of the user medicine, which are read by the server 200 based on the appearance of the user medicine by analyzing the medicine image.

The user's personal medicine information stored in the server 200 may include an image of the user medicine of which recognition training is performed by the server 200 in advance. The user's personal medicine information may include one or more pieces of information regarding the user medicine.

The server 200 may determine whether the medicine image recognition-requested by the medicine recognition requesting unit 120 corresponds to a user's personal medicine based on the user's personal medicine information stored in the server 200. If the server 200 determines that the recognition-requested medicine image corresponds to a user's personal medicine, the medicine information receiving unit 130 may receive at least one of a prescription history, a purchase history, a medicine-taking history, and a disease history of a user regarding the user medicine, from among pieces of the user's personal medicine information stored in the server 200.

If the server 200 determines that the recognition-requested medicine image does not correspond to a user's personal medicine, the medicine information receiving unit 130 may receive a recognition failure message from the server 200.

Although it is determined that the recognition-requested medicine image does not correspond to a user's personal medicine, if the recognition-requested medicine image is recognized based on non-prescription medicine information stored in the server 200, the medicine information receiving unit 130 may receive at least one of non-prescription medicine identification information and non-prescription medicine product information related to the user medicine, from among pieces of the non-prescription medicine information.

Figure 2:
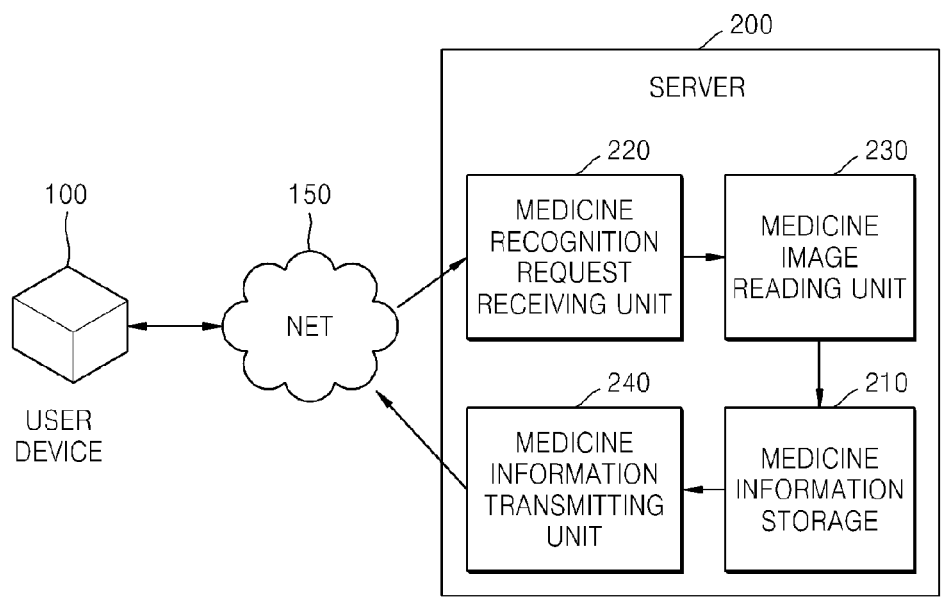
FIG. 2 is a block diagram of a server for providing a user's personal medicine information management service, according to an exemplary embodiment.

FIG. 2 is a block diagram of the server 200 for providing a user's personal medicine information management service, according to an exemplary embodiment.

The server 200 includes a medicine information storage 210, a medicine recognition request receiving unit 220, a medicine image reading unit 230, and a medicine information transmitting unit 240. As described above in relation to FIG. 1, the server 200 may perform data communication with the user device 100 via the wired or wireless communication network 150. Also, the server 200 may be a cloud computing based virtual server.

The medicine information storage 210 stores a user's personal medicine information. The medicine information storage 210 may further store information regarding non-prescription medicines.

A medicine image of a user medicine may include an image showing identification information readable from appearance of the user medicine, e.g., a medicine shape, a package shape, a medicine name, or a trademark, and an image showing product information readable from the appearance of the user medicine, e.g., a manufacturer name, a barcode, or a quick response (QR) code. A medicine image of a user's personal medicine includes a medicine image received from the user device 100.

The user's personal medicine information may include a medicine image as identification information of a user's personal medicine. Also, the user's personal medicine information may further include a medicine-taking history, a prescription history, a purchase history, a relate disease history, etc., regarding a user's personal medicine.

The medicine recognition request receiving unit 220 receives from the user device 100 a medicine image captured by photographing the appearance of a user medicine, as a request for recognition of the user medicine.

The medicine image reading unit 230 analyzes the received medicine image and reads the appearance and a remaining quantity of the user medicine. The medicine information transmitting unit 240 transmits to the user device 100 medicine quantity information and the user's personal medicine information stored in the server 200, based on a result of the reading by the medicine image reading unit 230.

The medicine image reading unit 230 may read identification information of the user medicine based on an image showing the appearance of the user medicine extracted from the medicine image. The image showing the appearance of the user medicine may be the identification information of the user medicine, or related identification information may be extracted by searching the user's personal medicine information stored in the server 200 by using the mage showing the appearance of the user medicine. The medicine information transmitting unit 240 may transmit the read identification information of the user medicine to the user device 100.

The medicine information transmitting unit 240 may transmit to the user device 100 the medicine quantity information read by the medicine image reading unit 230.

Also, the medicine information transmitting unit 240 may find a user's personal medicine corresponding to the medicine image by searching the user's personal medicine information stored in the server 200, based on the result of the reading by the medicine image reading unit 230. The medicine information transmitting unit 240 may transmit to the user device 100 additional information regarding the found user's personal medicine, e.g., product information, a medicine-taking history, and a prescription history.

The user's personal medicine information stored in the server 200 may include an image of the user medicine of which recognition training is performed by the server 200 in advance. The user's personal medicine information may include information regarding one or more user medicines.

The medicine image reading unit 230 may determine whether the medicine image recognition-requested by the user device 100 corresponds to a user's personal medicine, based on the user's personal medicine information stored in the medicine information storage 210. If the medicine image reading unit 230 determines that the recognition-requested medicine image corresponds to a user's personal medicine, the medicine information transmitting unit 240 may transmit at least one of a prescription history, a purchase history, a medicine-taking history, and a disease history of a user regarding the user medicine, from among pieces of the user's personal medicine information stored in the server 200.

If the medicine image reading unit 230 determines that the recognition-requested medicine image does not correspond to a user's personal medicine, the medicine information transmitting unit 240 may transmit a recognition failure message to the user device 100.

However, even when the recognition-requested medicine image is determined not to correspond to a user's personal medicine, if the recognition-requested medicine image is recognizable based on non-prescription medicine information stored in the medicine information storage 210, the medicine information transmitting unit 240 may transmit at least one of non-prescription medicine identification information and non-prescription medicine product information regarding the user medicine from among pieces of the non-prescription medicine information.

The server 200 may further include a personal medicine information processing unit (not shown) for setting the user's personal medicine information. The medicine information storage 210 may update a medicine-taking history from among pieces of the user's personal medicine information based on the medicine quantity information read from the medicine image.

In order to allow the server 200 to manage the user's personal medicine information by recognizing the user medicine, and to manage information regarding medicines useful to the user, the server 200 needs to recognize user's personal medicines in advance. For this, the server 200 may perform recognition training of the user's personal medicines with the aid of the user device 100.

A user device 300 for requesting and a server 400 for performing recognition training of a user medicine in order to provide a user's personal medicine information management service will now be described with reference to FIGS. 3 and 4.

Figure 3:
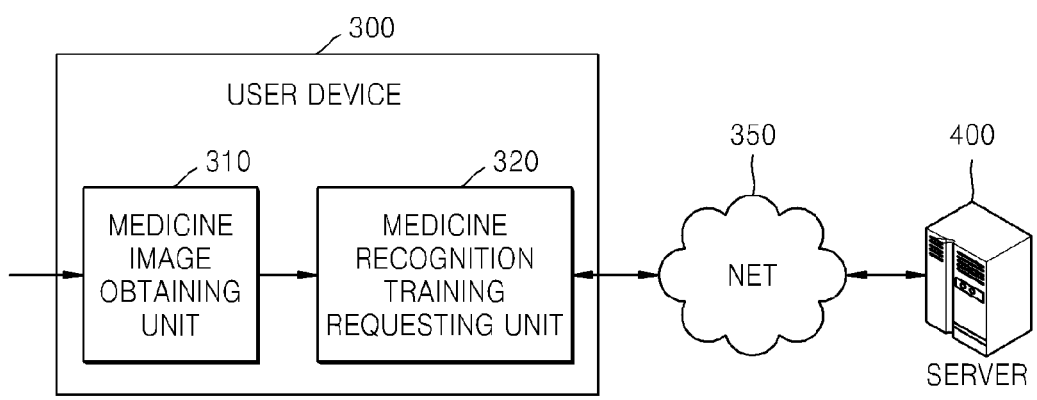
FIG. 3 is a block diagram of a user device for requesting recognition training of a user medicine in order to provide a user's personal medicine information management service, according to an exemplary embodiment.

FIG. 3 is a block diagram of the user device 300 for requesting recognition training of a user medicine in order to provide a user's personal medicine information management service, according to an exemplary embodiment.

The user device 300 includes a medicine image obtaining unit 310 and a medicine recognition training requesting unit 320. The user device 300 may perform data communication with the server 400 via a wired or wireless communication network 350. Also, the server 400 may be a cloud computing based virtual server.

The medicine image obtaining unit 310 may obtain a medicine image captured by photographing appearance of a user medicine. If an image sensor is included, the medicine image obtaining unit 310 may directly photograph the appearance of the user medicine. If an image sensor is not included, the medicine image obtaining unit 310 may obtain the medicine image captured by an accessible external device, such as a ubiquitous or Bluetooth device.

The medicine recognition training requesting unit 320 transmits to the server 400 the medicine image obtained by the medicine image obtaining unit 310, as a request for recognition training of the user medicine. The user medicine of which recognition training is completed by the server 400 may be added into user's personal medicine information stored in the server 400.

The medicine image obtaining unit 310 may obtain a plurality of different medicine images captured by repeatedly photographing the user medicine until the recognition training of the user medicine is completed by the server 400, and the medicine recognition training requesting unit 320 may repeatedly transmit the obtained medicine images. The user device 300 may receive from the server 400 a training completion message informing that the recognition training of the user medicine is completed.

The obtained medicine image of the user medicine may include images showing the appearance of the user medicine, e.g., an image showing a shape of a medicine itself, and an image showing a shape of a medicine package. Also, the medicine image of the user medicine may include at least one of an image showing non-prescription medicine identification information of the user medicine, and an image showing non-prescription medicine product information of the user medicine, which are readable from the appearance of the user medicine.

Like the user device 100, the user device 300 may transmit a request for recognition of the user medicine after the recognition training of the user medicine is completed by the server 400. In response to the request, the user device 300 may receive medicine quantity information and user's personal medicine information from the server 400 based on a result of the recognition of the user medicine.

Accordingly, if the request for the recognition of the user medicine is transmitted to the server 400, it is determined whether the recognition-requested medicine is a user's personal medicine, based on the user's personal medicine information stored in the server 400, and the user device 300 may receive from the server 400 a determination result message.

Figure 4:
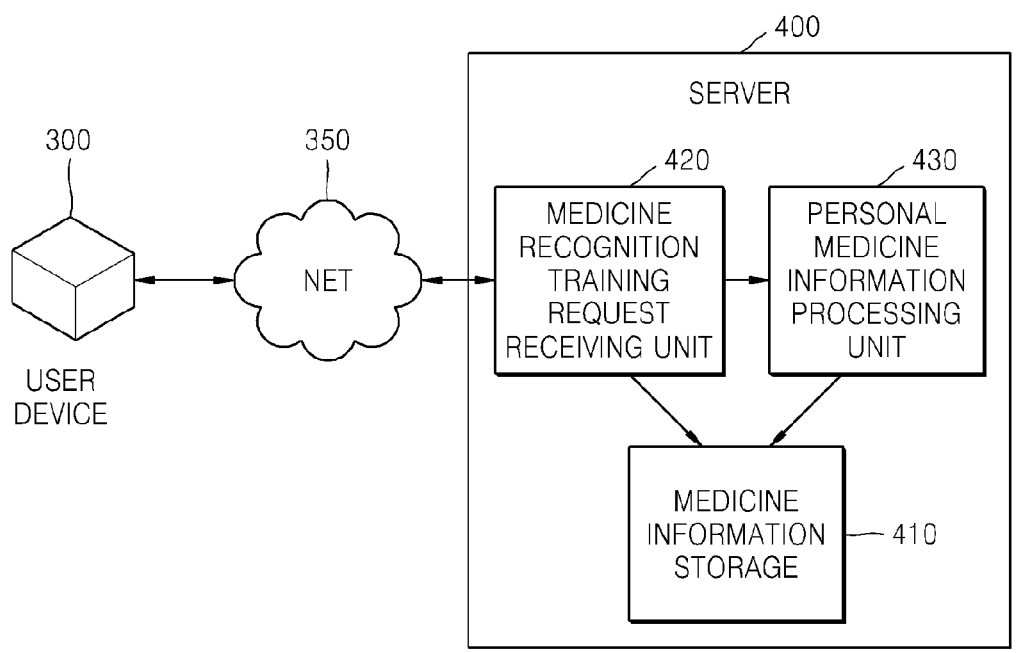
FIG. 4 is a block diagram of a server for performing recognition training of a user medicine in order to provide a user's personal medicine information management service, according to an exemplary embodiment.

FIG. 4 is a block diagram of the server 400 for performing recognition training of a user medicine in order to provide a user's personal medicine information management service, according to an exemplary embodiment.

The server 400 includes a medicine information storage 410, a medicine recognition training request receiving unit 420, and a personal medicine information processing unit 430. As described above in relation to FIG. 3, the server 400 may perform data communication with the user device 300 via the wired or wireless communication network 350. Also, the server 400 may be a cloud computing based virtual server.

The medicine information storage 410 stores user's personal medicine information. The medicine information storage 410 may further include information regarding non-prescription medicines.

A medicine image of a user medicine may include an image showing identification information readable from appearance of the user medicine, e.g., a medicine shape, a package shape, a medicine name, or a trademark, and an image showing product information readable from the appearance of the user medicine, e.g., a manufacturer name, a barcode, or a quick response (QR) code. Also, the medicine image itself may be stored as the user's personal medicine information. A medicine image of a user's personal medicine includes a medicine image received from the user device 300.

The medicine recognition training request receiving unit 420 may receive from the user device 300 a medicine image captured by photographing appearance of a user medicine, as a request for recognition training of the user medicine.

The medicine recognition training request receiving unit 420 may repeatedly receive a plurality of different medicine images captured by photographing the user medicine until the recognition training of the user medicine is completed. The medicine recognition training request receiving unit 420 may check whether the received medicine image is included in the user's personal medicine information stored in the medicine information storage 410. If the received medicine image is not included in the user's personal medicine information, the medicine recognition training request receiving unit 420 may perform the recognition training by using received medicine image.

The personal medicine information processing unit 430 may add the user medicine of which recognition training is completed, into the user's personal medicine information of the medicine information storage 410 based on the medicine image received by the medicine recognition training request receiving unit 420.

If the personal medicine information processing unit 430 adds the user medicine of which recognition training is completed to the user's personal medicine information, the server 400 may transmit to the user device 300 a training completion message informing that the recognition training of the user medicine is completed.

After that, the server 400 may receive from the user device 300 a medicine image captured by photographing appearance of the user medicine of which recognition training is completed, as a request for recognition of the user medicine. As such, the server 400 may analyze the received medicine image, may read the appearance and a remaining quantity of the user medicine, and may transmit to the user device 300 medicine quantity information and the user's personal medicine information stored in the server 400.

Accordingly, if the request for recognition of the user medicine is received from the user device 100, the server 400 may determine whether the recognition-requested medicine is a user's personal medicine based on the user's personal medicine information stored in the medicine information storage 410, and may transmit a determination result message to the user device 100.

Hereinabove, the user device 100 for requesting the server 200 for recognition of a user medicine, and the server 200 for recognizing the user medicine and providing user's personal medicine information, in order to provide a user's personal medicine information management service, are described with reference to FIGS. 1 and 2. The user device 300 for requesting the server 400 for recognition training of a user medicine, and the server 400 for performing the recognition training of the user medicine, in order to provide a user's personal medicine information management service, are described with reference to FIGS. 3 and 4.

Although the user device 100 and the server 200 are described separately from the user device 300 and the server 400 for convenience of explanation, the user device 100 for requesting for recognition of a user medicine and the user device 300 for requesting for recognition training of a user medicine may not be separated into different devices and may be integrated into one device.

Likewise, the server 200 for recognizing a user medicine and the server 400 for performing recognition training of a user medicine may not be separated into different servers and may be integrated into one server.

The user device 100 or 300 and the server 200 or 400 may identify a user medicine based on appearance of the user medicine if a user does not accurately know the name and use of the user medicine. In a user's personal medicine information management service according to an exemplary embodiment, a user medicine may be managed based on appearance of the user medicine, and product information such as ingredients, effects, and dosage instructions of the user medicine and personal medication information, such as a medicine-taking history and a prescription history of a user may be provided to the user.

Figure 5:
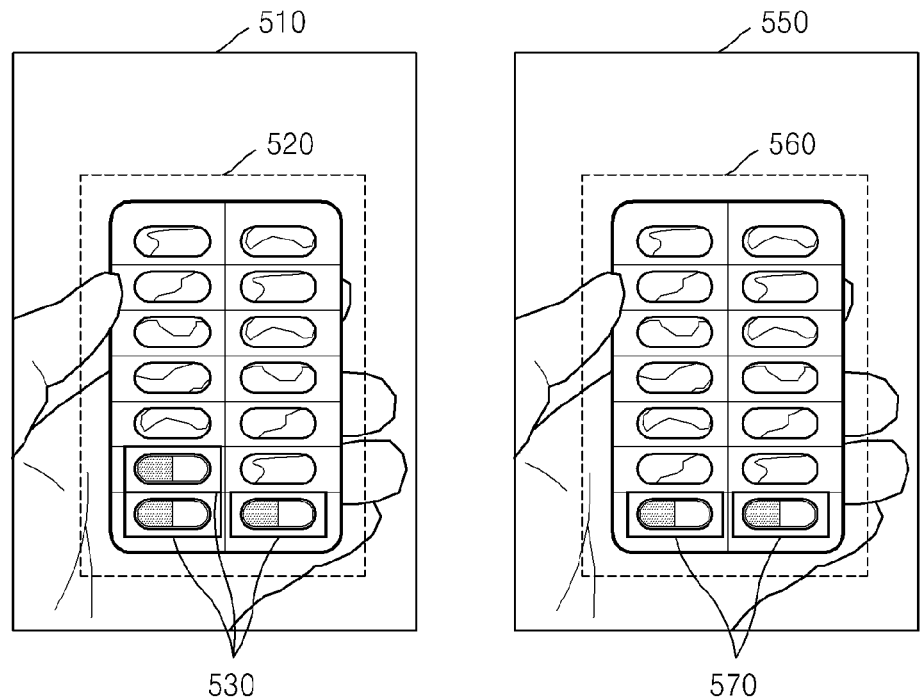
FIG. 5 illustrates medicine images captured by a user device and recognized by a server, according to an exemplary embodiment.

FIG. 5 illustrates medicine images 510 and 550 captured by a user device and recognized by a server, according to an exemplary embodiment. FIG. 5 will be described in conjunction with FIGS. 1 through 4.

The user device 300 may obtain the medicine images 510 and 550 of user medicines 530 and 570 to request the server 400 for recognition training of the user medicines 530 and 570. The user device 300 may directly capture the medicine images 510 and 550 by using a mounted image sensor. Alternatively, the user device 300 may obtain the medicine images 510 and 550 captured by a different device.

The user device 300 may transmit the medicine images 510 and 550 to the server 400 as a request for the recognition training of the user medicines 530 and 570. The server 400 performs the recognition training with respect to visual information readable from appearances of the user medicines 530 and 570. For example, the server 400 may perform recognition training of the user medicines 530 and 570 based on appearances of medicine packages 520 and 560 or the user medicines 530 and 570 themselves in the medicine images 510 and 550.

If the recognition training using the medicine images 510 and 550 is completed by the server 400, the medicine images 510 and 550 may be used as user's personal medicine information of the user medicines 530 and 570. The medicine images 510 and 550, the medicine packages 520 and 560, and the user medicines 530 and 570 themselves may be registered in the user's personal medicine information as identification information of user's personal medicines. The identification information of user's personal medicines may also include the names of the user's personal medicines. The names of the user's personal medicines may be arbitrarily input by a user.

Also, the user device 100 may obtain the medicine images 510 and 550 to request the server 200 for recognition of the user medicines 530 and 570. The user device 100 may directly capture the medicine images 510 and 550 by using an included image sensor.

The user device 100 may transmit the medicine images 510 and 550 to the server 200 as a request for recognition of the user medicines 530 and 570. The server 200 analyzes the medicine images 510 and 550 and reads the types and quantities of the user medicines 530 and 570.

The server 200 analyzes visual information readable from the appearances of the user medicines 530 and 570 in the medicine images 510 and 550. For example, the server 200 may extract the appearances of the medicine packages 520 and 560 or the user medicines 530 and 570 themselves in the medicine images 510 and 550, and may search the user's personal medicine information stored in the server 200 to find related information. If information regarding the user medicines 530 and 570 is found from the user's personal medicine information, the server 200 may transmit the stored information to the user device 100 as the user's personal medicine information. Also, the server 200 may update a medicine-taking history from among pieces of the user's personal medicine information stored in the server 200 by using the quantities of the user medicines 530 and 570 read from the medicine images 510 and 550.

The appearances of the user medicines 530 and 570 read from the medicine images 510 and 550 by the server 200 or 400 may include the shapes, sizes, colors, surface-engraved/embossed, or printed text or figures of pills or tablets. Also, the appearances of the medicine packages 520 and 560 read from the medicine images 510 and 550 by the server 200 or 400 may include capsule colors, aluminum-coated soft plastic package shapes, box shapes, bottle shapes, bag shapes, sizes, colors, surface-engraved/embossed, or printed text or figures of the medicine packages 520 and 560.

Figure 6:
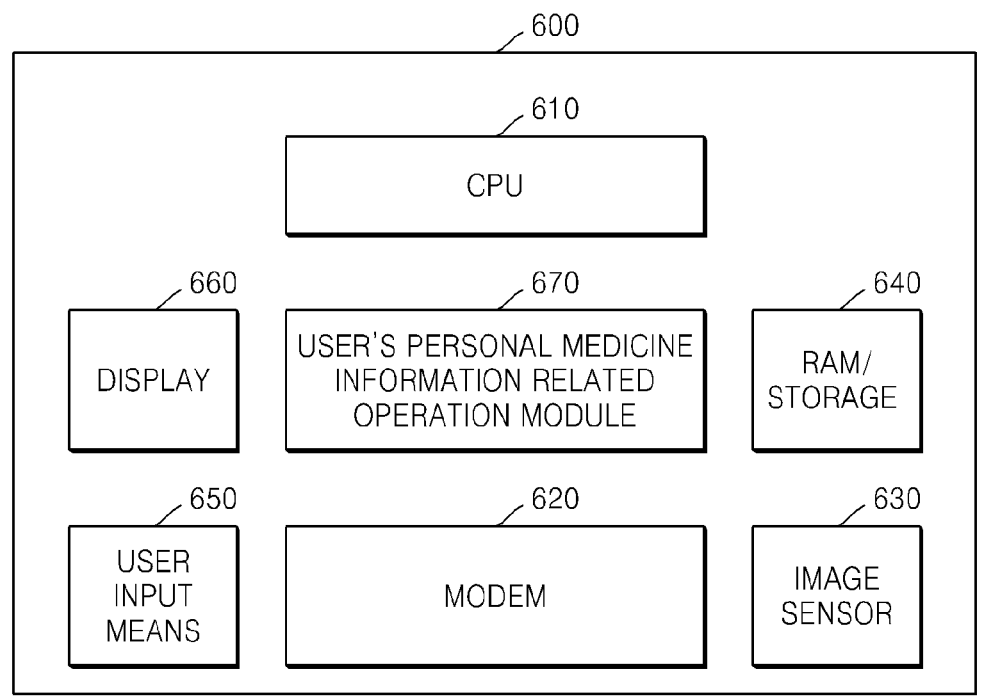
FIG. 6 is a detailed block diagram of a user device for providing a user's personal medicine information management service, according to an exemplary embodiment.

FIG. 6 is a detailed block diagram of a user device 600 for providing a user's personal medicine information management service, according to an exemplary embodiment.

The user device 600 includes a central processing unit (CPU) 610, a modem 620, an image sensor 630, a random access memory (RAM)/storage 640, a user input means 650, a display 660, and a user's personal medicine information related operation module 670.

The CPU 610 controls operations of the modem 620, the image sensor 630, the RAM/storage 640, the user input means 650, the display 660, and the user's personal medicine information related operation module 670, in order to receive the user's personal medicine information management service provided by the server 200 or 400 illustrated in FIG. 2 or 4. The modem 620 may support wired data communication or wireless data communication based on a wireless communication standard such as a 3rd generation (3G) or long term evolution (LTE) standard. The user's personal medicine information related operation module 670 may perform wireless data communication with the server 200 or 400 via the modem 620.

The user device 600 is an example in which the user devices 100 and 300 illustrated in FIGS. 1 and 3 are integrated.

In order to provide a user's personal medicine information management service, the user's personal medicine information related operation module 670 may perform an operation of transmitting a medicine image to the server 200 as a request for recognition of a user medicine, and an operation of transmitting a medicine image to the server 400 as a request for recognition training of a user medicine.

In more detail, a request for capturing of a medicine image, a request for recognition training of a user medicine, a request for recognition of a user medicine, and a request for checking user's personal medicine information may be input by a user via the user input means 650.

Based on a request for capturing of a medicine image input via the user input means 650, the user's personal medicine information related operation module 670 may call the image sensor 630 to capture the medicine image of a user medicine.

Based on a request for recognition training of a user medicine input via the user input means 650, the user's personal medicine information related operation module 670 may transmit to the server 200 the medicine image captured by the image sensor 630, and may display on the display 660 a response received from the server 200.

Based on a request for recognition of a user medicine input via the user input means 650, the user's personal medicine information related operation module 670 may transmit to the server 400 the medicine image captured by the image sensor 630, and may display on the display 660 a response received from the server 400.

Also, the user's personal medicine information received from the server 200 or 400 may be stored in the RAM/storage 640.

Figure 7A:
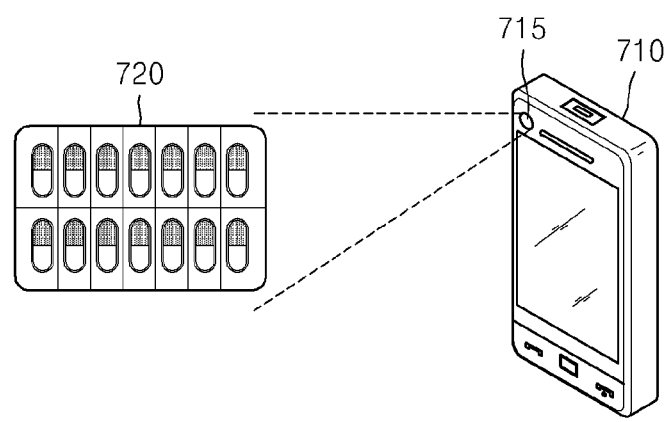
FIGS. 7A, 7B, and 7C illustrate various examples of the user device illustrated in FIG. 1 or 3, according to exemplary embodiments.
Figure 7B:
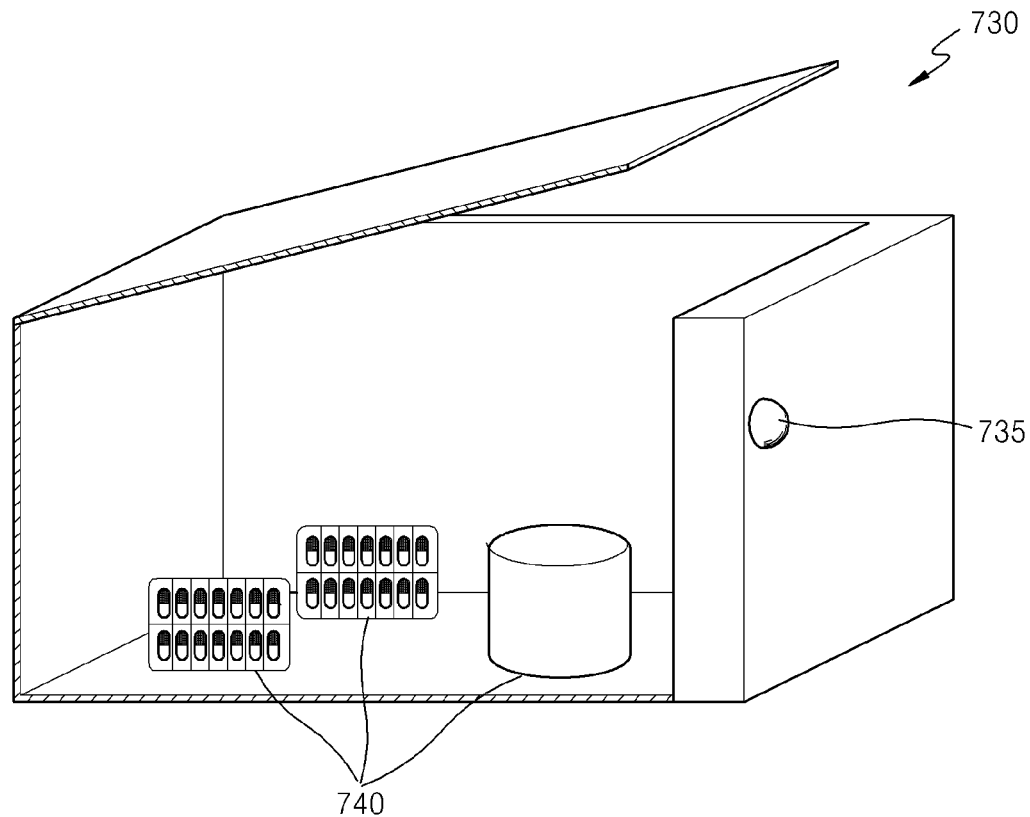
Figure 7C:
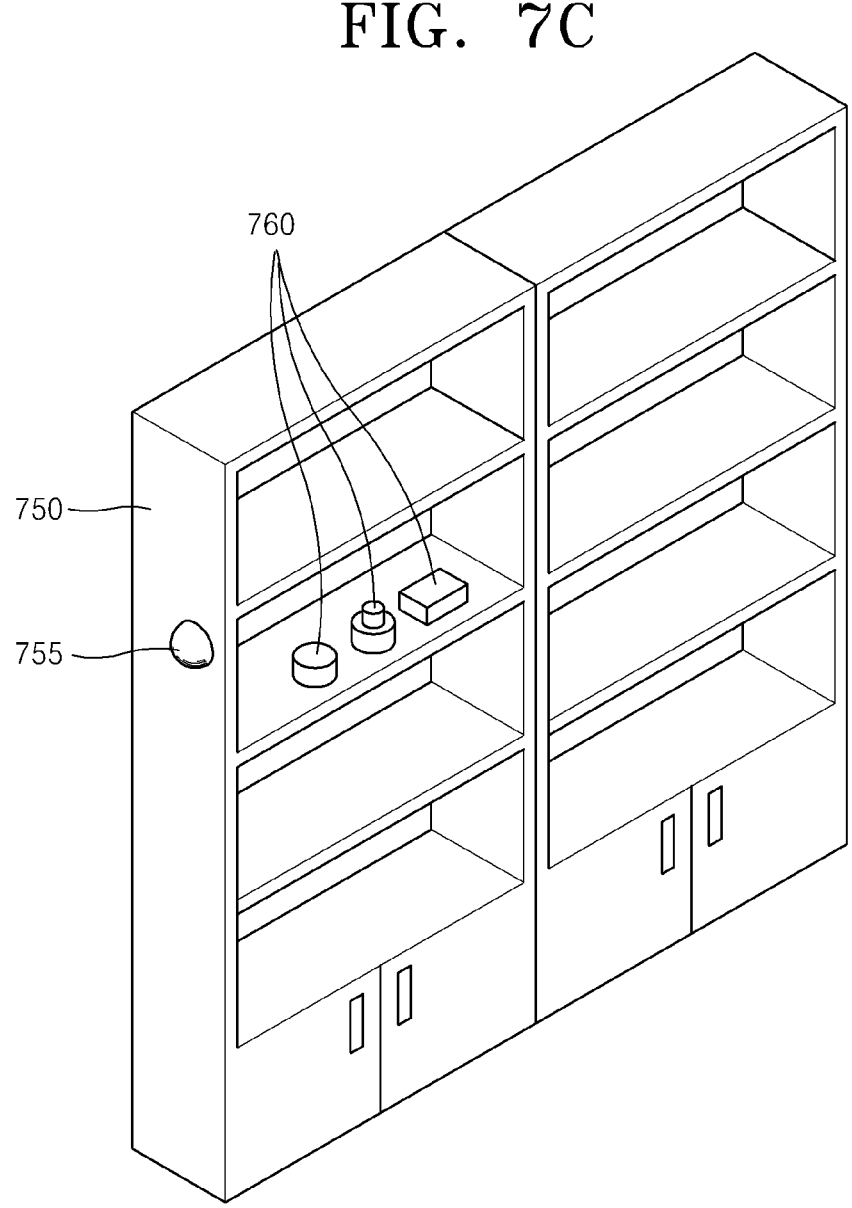

FIGS. 7A, 7B, and 7C illustrate various examples of the user device 100 or 300 illustrated in FIG. 1 or 3, according to exemplary embodiments.

The user device 100 or 300 may be a portable device 710, a medicine chest 730, or a medicine cabinet 750.

For example, the portable device 710 may include a mobile phone, a smart phone, or a tablet personal computer (PC) on which an image sensor 715 is mounted. A user may manipulate the portable device 710 to capture a medicine image by photographing a user medicine 720 and may transmit the medicine image to the server 200 or 400 illustrated in FIG. 2 or 4. A response received from the server 200 or 400 may be displayed on the portable device 710.

Alternately, an image sensor 735 may be mounded on the medicine chest 730. A user may take one of user medicines 740 out of the medicine chest 730 and place the medicine 740 close to the image sensor 735 to capture a medicine image. The medicine image captured by manipulating the medicine chest 730 may be transmitted to the server 200 or 400. A response received from the server 200 or 400 may be displayed on a display of the medicine chest 730, or may be transmitted to and displayed on a different user device. For example, the server 400 may receive from the medicine chest 730 a request for recognition of one of the user medicines 740, and may transmit to a television (TV) user's personal medicine information regarding the recognized user medicine 740, and the user may check the user's personal medicine information on the TV.

Still further, an image sensor 755 may be mounted on the medicine cabinet 750, and a user may bring one of user medicines 760 out of the medicine cabinet 750 close to the image sensor 755 to capture a medicine image. As such, the medicine cabinet 750 may scan one of the user medicines 760 kept in the medicine cabinet 750 and selected by the user, by using the image sensor 755. The captured medicine image may be transmitted to the server 200 or 400, and a response received from the server 200 or 400 may be displayed on a display of the medicine cabinet 750, or may be transmitted to and displayed on a different user device.

The user device 100, 300, or 600 illustrated in FIG. 1, 3, or 6 may be manufactured as an independent device. If medicines are kept in a general box or cabinet, the independent user device 100, 300, or 600 may be installed on or adhered to the box or cabinet to capture and transmit a medicine image to a server, thereby providing a user's personal medicine information management service.

Figure 8A:
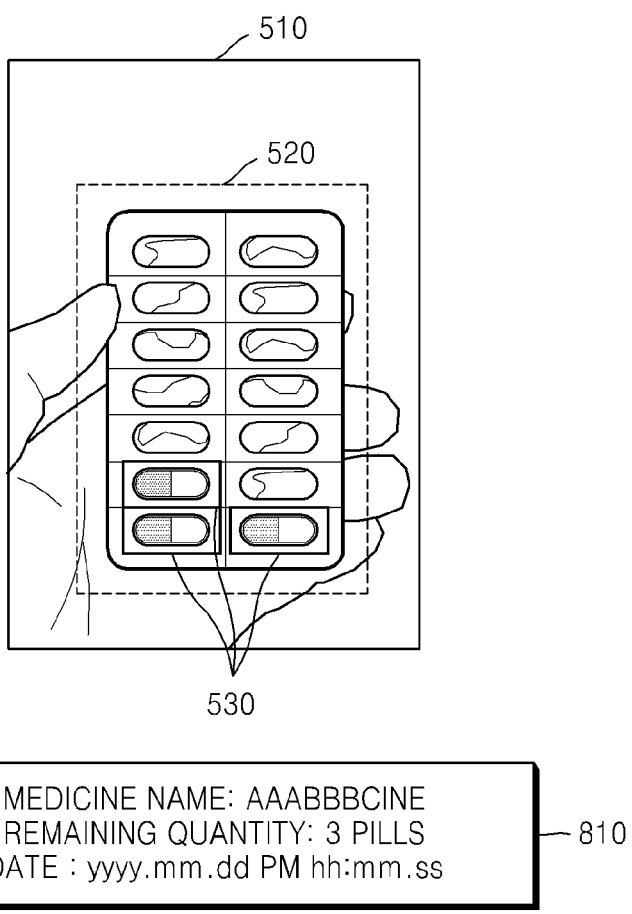
FIGS. 8A and 8B illustrate screens for displaying user's personal medicine information, according to exemplary embodiments.
Figure 8B:
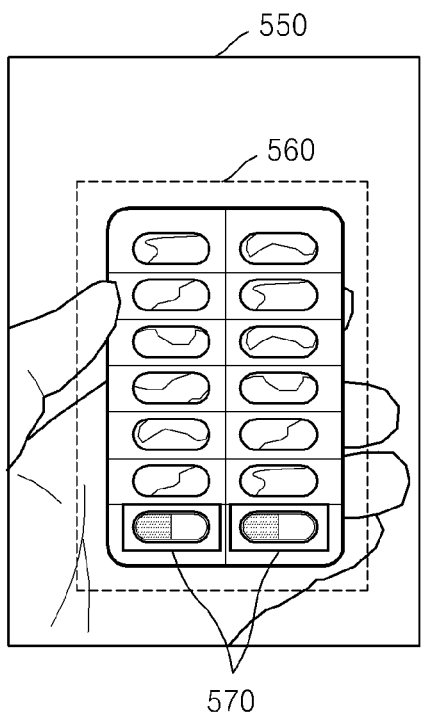

FIGS. 8A and 8B illustrate screens for displaying user's personal medicine information, according to exemplary embodiments. FIGS. 8A and 8B will be described in conjunction with FIGS. 1 through 6.

The server 400 may receive the medicine image 510 from the user device 100 or 600 as a request for recognition of the user medicine 530. The server 400 may analyze the medicine image 510 and may check whether information regarding the user medicine 530, which is read from the medicine image 510, is included in user's personal medicine information stored in the medicine information storage 410. The server 400 may adjust a search option whether to search the user's personal medicine information stored in the medicine information storage 410 for a medicine image identical or similar to an image of the medicine package 520 or the user medicine 530 recognized from the medicine image 510.

If it is checked that the information regarding the user medicine 530 corresponding to the medicine image 510 is stored in the medicine information storage 410, based on the image of the medicine package 520 or the user medicine 530 recognized from the medicine image 510, the server 400 may extract identification information, such as the type and name of the user medicine 530, from the stored user's personal medicine information.

The medicine information storage 410 may store information regarding user's personal medicines, which is registered as the user's personal medicine information, by performing recognition training of user medicines, and may further store product information regarding nonprescription medicines sold on the market. Accordingly, although the information regarding the user medicine 530 of which recognition is requested is not included in the user's personal medicine information stored in the medicine information storage 410, if a non-prescription medicine identical to the user medicine 530 is detected from the product information regarding non-prescription medicines, identification information regarding the non-prescription medicine may be extracted.

Also, the server 400 may analyze the medicine image 510 and may read a remaining quantity of the user medicine 530. The server 400 may transmit the extracted identification information and remaining quantity information of the user medicine 530 to the user device 100 or 600.

Also, if a time when recognition of the user medicine 530 is requested by a user or a time when the recognition of the user medicine 530 is transmitted by the server 400 corresponds to a time when the user takes the user medicine 530, information regarding the time when the recognition of the user medicine 530 is requested or transmitted may be transmitted to the user device 100 or 600. Accordingly, the server 400 may transmit information regarding a medicine name, a remaining quantity, and a server response time or (a recognition request time) read from the medicine image 520, in response to the request for the recognition of the medicine image 510.

The user device 100 or 600 may receive the information read from the medicine image 520 and may form a medicine information window 810 to display the information on a display screen.

Also, the server 400 may update a medicine-taking history from among pieces of the user's personal medicine information based on the remaining quantity of the user medicine 530 read from the medicine image 520.

As another example, if the user device 100 or 600 sequentially requests for recognition of the medicine images 510 and 550, the server 400 may analyze the medicine images 510 and 550 and may determine the medicine image 550 indicating a smaller remaining quantity, as an image after the user takes the user medicine 570. As such, the server 400 may determine a time for requesting recognition of the medicine image 550, as a medicine-taking time, and may update the medicine-taking history from among pieces of the user's personal medicine information.

Also, the server 400 may transmit information read from the medicine image 550, together with medicine identification information, remaining quantity information, and response time information, in response to the request for the recognition the medicine image 550. Furthermore, the server 400 may further transmit additional information, e.g., product information, such as ingredients and effects of the user medicine 570, and personal medication information, such as a medicine-taking history and a prescription history of the user, which is included in the user's personal medicine information stored in the medicine information storage 410, in response to the request for the recognition the medicine image 550.

The user device 100 or 600 may receive the information read from the medicine image 550, and the additional information, such as ingredients, effects, a medicine-taking history, and may form a medicine information window 850 to display the information and the additional information on a display screen.

Since a personal history of the user, e.g., a medicine-taking history, may be displayed in the medicine information window 850, the user's private life may be revealed. Referring to FIGS. 7A, 7B, and 7C, although the portable device 710 is the user's personal product and thus is used personally, the medicine chest 730 or the medicine cabinet 750 may be easily accessed by other people. Accordingly, the server 200 or 400 may set authority to access the user's personal medicine information in order to protect the user's private life. In this case, the server 200 or 400 may provide the user's personal medicine information including the medicine-taking history of the user upon a request of only the authorized user device 100, 300, or 600.

A medicine recognition training method to provide a user's personal medicine information management service by a user device, by a server, and by the user device and the server will now be described with reference to FIGS. 9 through 11 in conjunction with the FIGS. 3 and 4.

FIG. 9 is a flowchart 900 of a method of requesting recognition training of a user medicine by the user device 300 to provide a user's personal medicine information management service, according to an exemplary embodiment.

In operation 910, in order to provide the user's personal medicine information management service via the server 400, the user device 300 obtains a medicine image captured by photographing appearance of a user medicine. The appearance of the user medicine covers a medicine, a medicine package, a medicine bottle, a medicine box, a medicine bag, etc.

In operation 920, the user device 300 transmits the obtained medicine image to the server 400 as a request for recognition training of the user medicine. The user device 300 may repeatedly transmit to the server 400 a plurality of different medicine images captured by photographing the user medicine until a training completion message is received from the server 400.

FIG. 10 is a flowchart 1000 of a method of performing recognition training of a user medicine by the server 400 to provide a user's personal medicine information management service, according to an exemplary embodiment.

In operation 1010, the server 400 receives from the user device 300 a medicine image captured by photographing appearance of a user medicine, as a request for recognition training of the user medicine. In operation 1020, the server 400 may add the user medicine into user's personal medicine information based on the received medicine image. The server 400 may analyze the received medicine image, may extract an image showing the appearance of the user medicine, and may store the showing the appearance of the user medicine as the user's personal medicine information of the user medicine.

Figure 11A:
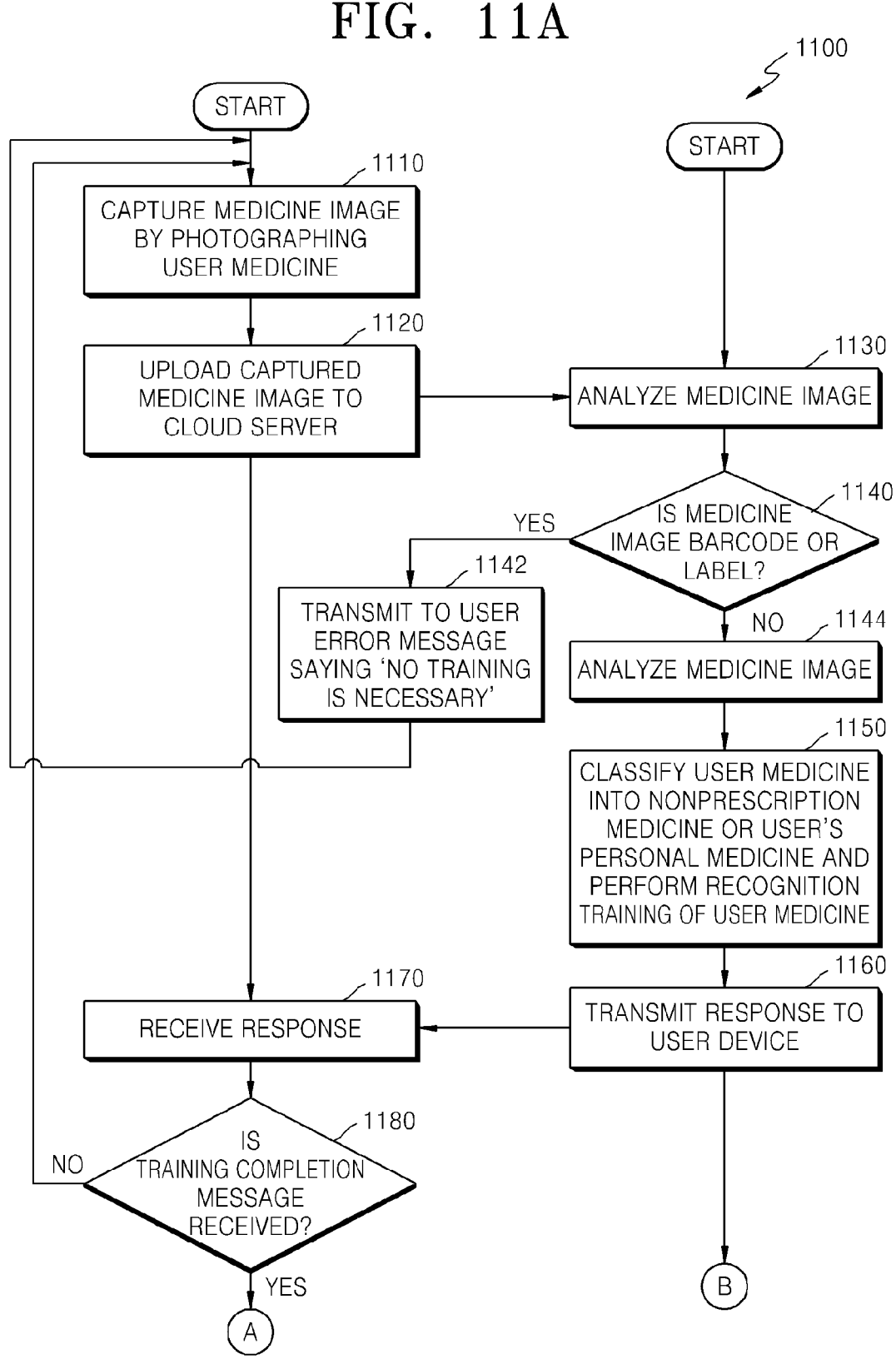
FIGS. 11a and 11b are flowcharts of a method of requesting and performing recognition training of a user medicine by a user device and a server to provide a user's personal medicine information management service, according to an exemplary embodiment.
Figure 11B:
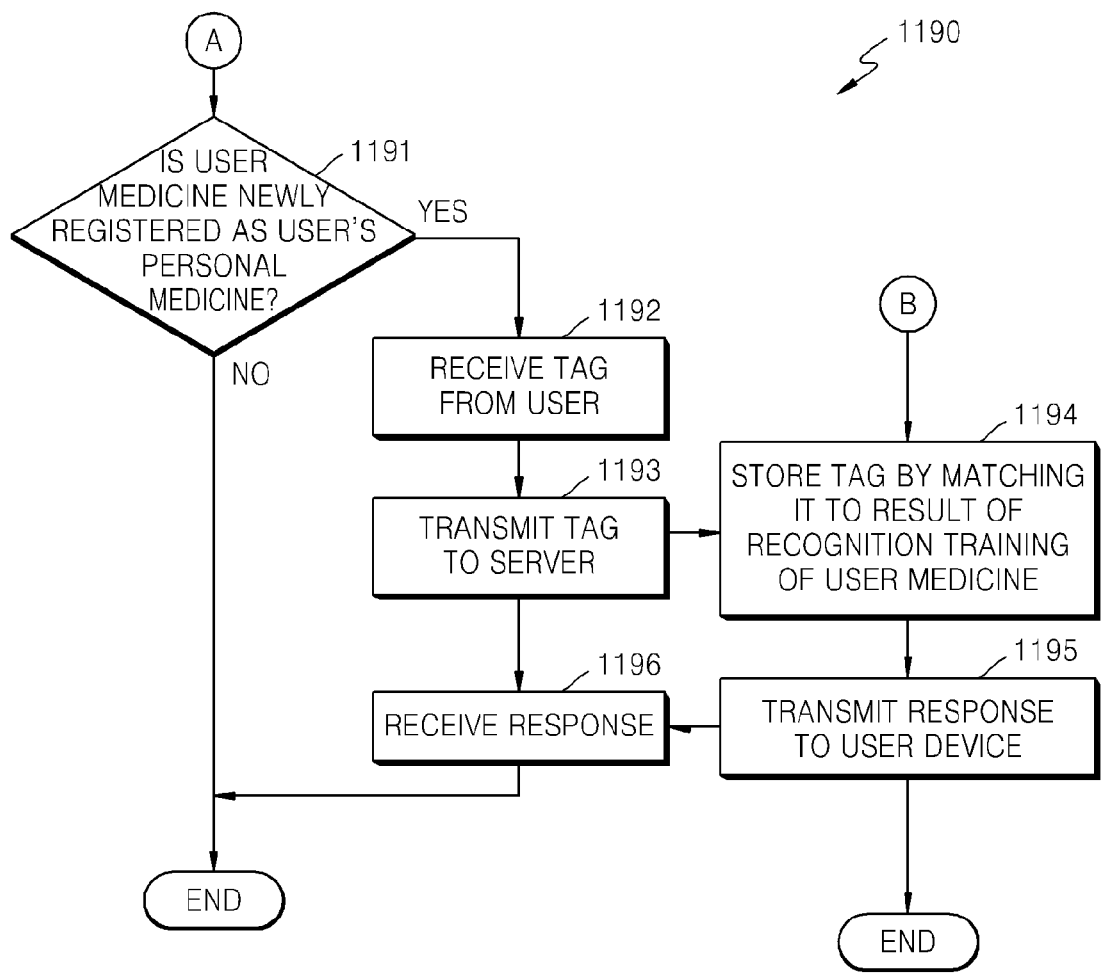

FIGS. 11a and 11b are flowcharts 1100 and 1190 of a method of requesting and performing recognition training of a user medicine by the user device 300 and the server 400 to provide a user's personal medicine information management service, according to an exemplary embodiment.

In operations 1110 and 1120, a user captures a medicine image by photographing a user medicine by using the user device 300 and uploads the captured medicine image to the server 400, e.g., a cloud server. As such, a request for recognition training of the user medicine may be transmitted to the server 400.

In operation 1130, the server 400 may analyze the medicine image received from the user device 300. Methods of analyzing the medicine image and recognizing the user medicine may differ according to the type of the medicine image. For example, the server 400 may determine whether the medicine image is an image of a barcode or a label (operation 1140).

If the medicine image is an image of a barcode or a label, the server 400 may recognize the user medicine by reading the barcode or the label. However, in this case, since the recognition training of the user medicine is not necessary, an error message such as 'No training is necessary' may be transmitted to the user device 300 (operation 1142).

If it is determined in operation 1140 that the medicine image is not an image of a barcode or a label, it is assumed that the medicine image includes an image showing appearance of the user medicine, and the image showing the appearance of the user medicine may be extracted and analyzed (operation 1144). The recognition training of the user medicine may be performed by analyzing the image showing the appearance of the user medicine. A result of the recognition training of the user medicine may be stored in a storage related to a medicine appearance recognition module of the server 400. Also, the image showing the appearance of the user medicine read from the medicine image may be stored in the server 400.

In operation 1150, if the recognition training of the user medicine is completed by the server 400, the user medicine may be classified into a non-prescription medicine or a user's personal medicine. The user medicine of which the recognition training is completed by the server 400 may be classified into a user's personal medicine and may be additionally registered in user's personal medicine information as a new personal medicine. Alternatively, if the user medicine of which the recognition training is completed by the server 400 is classified into a non-prescription medicine based on information regarding non-prescription medicines purchasable on the market, the user medicine may be registered in the user's personal medicine information as a non-prescription medicine.

In operation 1160, the server 400 may transmit to the user device 300 a message informing that the recognition training of the user medicine is completed or a message informing that the user medicine is registered as a user's personal medicine or a nonprescription medicine, as a response.

In operation 1180, the user device 300 may check whether a training completion message is received, based on the response of the server 400 received in operation 1170. If the recognition training is completed, an operation for the recognition training of the user medicine between the user device 300 and the server 400 is completed. If the recognition training is not completed, the method returns to operation 1110, and a new medicine image may be captured by photographing the user medicine and may be transmitted as a new request for the recognition training of the user medicine.

The user may allocate tags for identifying user's personal medicines including the user medicine of which recognition training is completed by the server 400 and which is added into the user's personal medicine information as a new personal medicine in operation 1150. An operation of allocating tags to user's personal medicines between the user device 300 and the server 400 may be performed according to the flowchart 1190.

In operation 1191, the user device 300 may check whether the user medicine is newly registered as a user's personal medicine in the user's personal medicine information of the server 400. In operation 1192, if the user medicine is newly registered as a user's personal medicine, the user device 300 may receive a unique tag for identifying the user's personal medicine from the user. In operation 1193, the user device 300 may transmit to the server 400 tag information of the newly added user's personal medicine. In operation 1194, the server 400 may store the received tag information by matching it to a result of the recognition training of the medicine appearance recognition module. In operations 1195 and 1196, the server 400 and the user device 300 may transmit and receive a message informing that a tag is completely allocated to the user's personal medicine that is newly registered in the user's personal medicine information.

A method of providing a user's personal medicine information management service by a user device, by a server, and by the user device and the server will now be described with reference to FIGS. 12 through 14, in conjunction with the FIGS. 1 and 2.

FIG. 12 is a flowchart 1200 of a method of providing a user's personal medicine information management service by the user device 100 via the server 200, according to an exemplary embodiment.

In operation 1210, the user device 100 obtains a medicine image captured by photographing appearance of a user medicine. The user device 100 may photograph a medicine or a medicine package. In operation 1220, the user device 100 transmits the medicine image to the server 200 as a request for recognition of the user medicine.

In operation 1230, the user device 100 receives medicine quantity information and user's personal medicine information from the server 200 based on a result of the recognition of the user medicine. If the user medicine is recognition-trained by the server 200 in advance and thus is already registered in the user's personal medicine information, identification information of the user medicine from among pieces of the user's personal medicine information may be received. Also, non-prescription medicine product information and personal medication information such as a medicine-taking history of the user from among pieces of the user's personal medicine information may be received.

FIG. 13 a flowchart 1300 of a method of providing a user's personal medicine information management service by the server 200, according to an exemplary embodiment.

In operation 1310, the server 200 receives from the user device 100 a medicine image captured by photographing appearance of a user medicine, as a request for recognition of the user medicine. In operation 1320, the server 200 analyzes the received medicine image and reads the appearance and a remaining quantity of the user medicine.

In operation 1330, the server 200 transmits to the user device 100 medicine quantity information and user's personal medicine information stored in the server 200, based on a result of the reading. That is, in addition to identification information and quantity information read from the medicine image, the server 200 may extract and transmit non-prescription medicine product information and personal medication information such as a medicine-taking history of the user from among pieces of the user's personal medicine information stored in the server 200.

Also, the server 200 may update the medicine-taking history from among pieces of the user's personal medicine information based on the medicine quantity information read from the medicine image.

Figure 14:
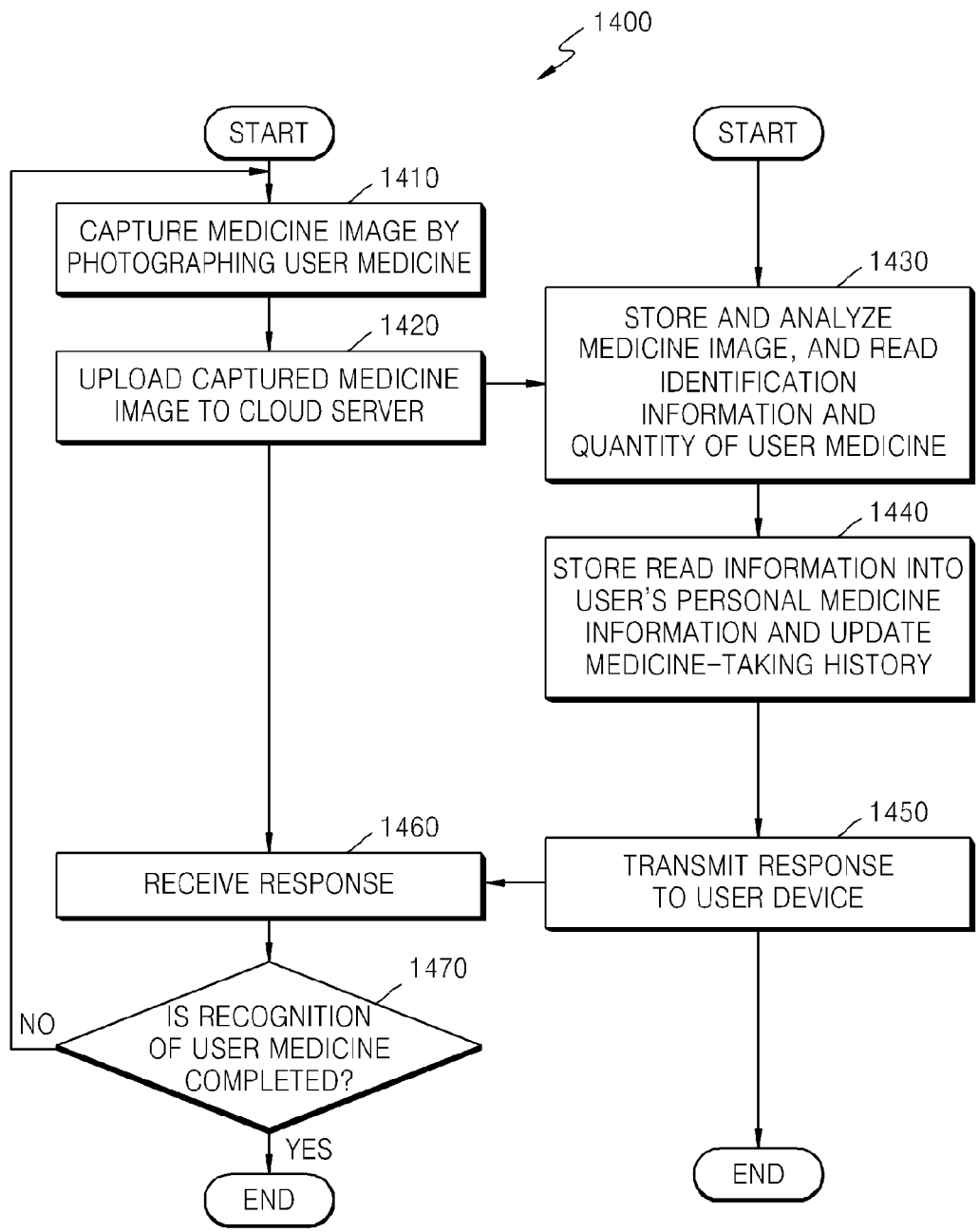
FIG. 14 is a flowchart of a method of providing a user's personal medicine information management service by a user device and a server, according to an exemplary embodiment.

FIG. 14 is a flowchart 1400 of a method of providing a user's personal medicine information management service by the user device 100 and the server 200, according to an exemplary embodiment.

In operation 1410, a user captures a medicine image by photographing a user medicine by using the user device 100 and uploads the captured medicine image to the server 200, e.g., a cloud server. As such, a request for recognition training of the user medicine may be transmitted to the server 200 in operation 1420.

In operation 1430, the server 200 stores and analyzes the received medicine image, and extracts an image showing appearance of the user medicine and reads a remaining quantity of the user medicine from the medicine image. The server 200 may read the image showing the appearance of the user medicine and may extract identification information of the user medicine. The server 200 may search user's personal medicine information and may check whether the read image showing the appearance of the user medicine is included in the user's personal medicine information.

In operation 1440, the server 200 may store quantity information read from the medicine image into the user's personal medicine information and may update a medicine-taking history of the user.

In operation 1450, the server 200 may transmit to the user device 100 the quantity information and the identification information read from medicine image, as a response. Also, the server 200 may extract product information or personal medication information, such as the medicine-taking history related to the user medicine from the user's personal medicine information, and may transmit the product information or the personal medication information to the user device 100.

In operations 1460 and 1470, the user device 100 may check whether the recognition of the user medicine is completed, based on the response of the server 200. If the recognition of the user medicine is completed, an operation of recognizing the user medicine between the user device 100 and the server 200 is completed. If the recognition of the user medicine is not completed, the method returns to operation 1410, and a new medicine image may be captured by photographing the user medicine and may be transmitted as a new request for the recognition of the user medicine.

Figure 15:
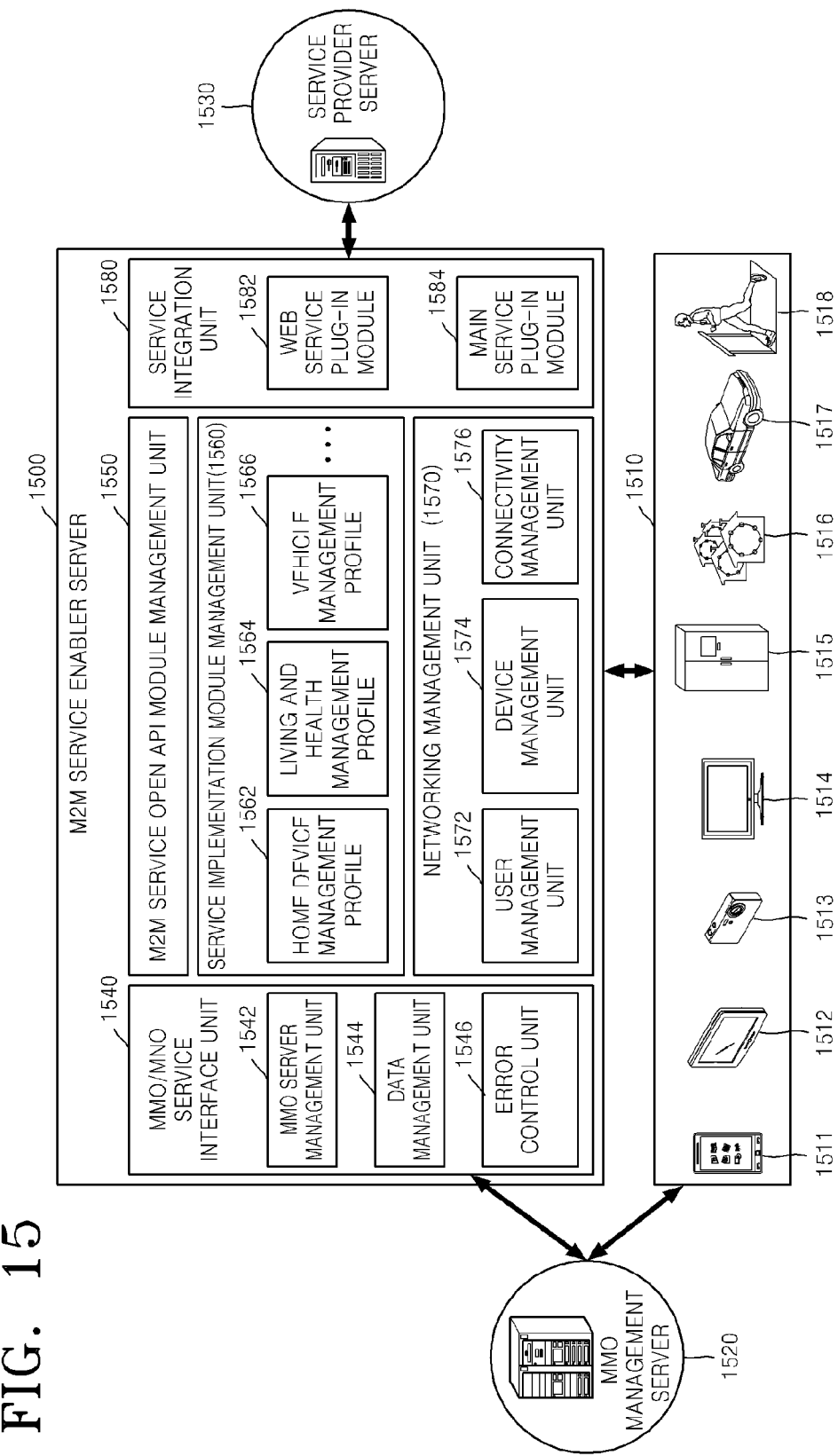
FIG. 15 is a block diagram of a convergence server for providing a machine-to-machine (M2M) service including a user's personal medicine information management service, according to an exemplary embodiment.

FIG. 15 is a block diagram of a convergence server 1500 for providing a machine-to-machine (M2M) service including a user's personal medicine information management service, according to an exemplary embodiment.

The server 1500 is a service enabling server for providing various M2M services between different devices by realizing an intelligent network for associating an Internet service with external communication networks of user devices 1510 including mobile terminals.

The server 1500 mainly includes an M2M mobile operator (MMO)/mobile network operator (MNO) service interface unit 1540, an M2M service open application programming interface (API) module management unit 1550, a service implementation module management unit 1560, a networking management unit 1570, and a service integration unit 1580.

The server 1500 may transmit and receive data to and from the user devices 1510 based on an M2M protocol. The user devices 1510 implement M2M communications based on an M2M protocol, and thus may include all devices capable of receiving various M2M services provided by the server 1500. For example, the user devices 1510 may include, for example, a smart phone 1511, a tablet PC 1512, a camera/camcorder 1513, a display device 1514 such as a TV, a kitchen appliance 1515 such as a refrigerator, a home network 1516 including a user's home network and an accessible external home network, a vehicle 1517, and an exercise equipment 1518.

The server 1500 performs data communication with an MMO management server 1520 of a communication carrier, which is located outside a home network and manages MMO or MNO services, via the MMO/MNO service interface unit 1540.

MMO/MNO service providers for operating the MMO/MNO services are mobile carriers for providing mobile communication services by using mobile communication networks constructed by other mobile carriers. An MMO/MNO service provider provides MMO/MNO services using existing mobile communication networks, makes profits from membership fees, call charges, and supplementary service charges of customers, and pays providers of the mobile communication networks for fees for using the mobile communication networks.

For example, the MMO/MNO service interface unit 1540 may transmit or receive device management information to or from the MMO management server 1520 based on an MMO specific protocol. The MMO/MNO service interface unit 1540 may include an MMO server management unit 1542 for managing at least one MMO management server 1520 that provides MMO/MNO services to the server 1500, and a data management unit 1544 and an error control unit 1546 for respectively managing and controlling data and errors generated while receiving services of the MMO management server 1520.

The MMO server management unit 1542 may provide a common interface for external MMO service providers who want to provide MMO/MNO services via the server 1500.

The networking management unit 1570 may include a user management unit 1572, a device management unit 1574, and a connectivity management unit 1576, and may manage user information, device information, and connectivity states to form a network with the user devices 1510. The networking management unit 1570 may observe and manage states of the user devices 1510, and may control operations of the user devices 1510.

The service integration unit 1580 integrates various services provided by a service provider server 1530, in order to integrally provide various M2M services. The service integration unit 1580 may include a main service plug-in module 1584 and a web service plug-in module 1582 in order to provide web services provided by external service providers as well as main services provided by an operator of the server 1500. Data communication with the service provider server 1530, e.g., an operation of downloading applications from the service provider server 1530, may be performed via the main service plug-in module 1584 and the web service plug-in module 1582. The web service plug-in module 1582 may provide a common interface for external service providers such as external website operators.

The M2M service open API module management unit 1550 of the server 1500 provides an M2M service interface in the form of an API as a common interface for integrating and organizing various M2M services provided to the user devices 1510. In order to be freely used by external service providers and to be functionally extended later, the M2M service interface may be provided in the form of an open API. Accordingly, service providers may implement M2M services such as mashup services by using the M2M service open API provided by the M2M service open API module management unit 1550, and the service integration unit 1580 may integrally manage M2M services of various service providers.

The service implementation module management unit 1560 may manage profiles for implementing various M2M services provided by the server 1500. The service implementation module management unit 1560 may manage service profiles such as web applications for implementing the main services and the external web services which are integrated by the service integration unit 1580.

The service implementation module management unit 1560 may provide a home device management profile 1562 for managing and controlling home devices of the user, a living and health management profile 1564 for managing information regarding living and health of the user and controlling related devices, and a vehicle management profile 1566 for managing various states of a vehicle of the user, e.g., driving, security, and maintenance states, as M2M services provided by the server 1500.

One of integrated M2M services provided by the server 1500 is the user's personal medicine information management service provided by the server 200 or 400 illustrated in FIG. 2 or 4. For example, the user's personal medicine information management service provided by the server 200 or 400 may be implemented by the living and health management profile 1564 of the server 1500, and the user device 100, 300, or 600 illustrated in FIG. 1, 3, or 6 are examples of the user devices 1510 and may implement the user's personal medicine information management service by using the living and health management profile 1564 of the server 1500.

The service implementation module management unit 1560 may generate a new service profile by combining individually implemented service profiles. For example, a refrigerator management service implemented by the home device management profile 1562 may provide a service for searching for food kept in a refrigerator, and a body fat management service implemented by the living and health management profile 1564 may provide a service for providing diet menus to reduce body fat of the user. Although the refrigerator management service and the body fat management service are basically implemented as separate services, the server 1500 may associate the refrigerator management service and the body fat management service with each other, and may implement a new service for searching for food for managing body fat of the user in the refrigerator.

Since other communication carriers may easily access a local network such as the home network of the user devices 1510 via the common interface for mobile carriers and the open API for service providers, which are provided by the server 1500, various convergence services in which the local network of the user devices 1510 is connected to and associated with external networks may be implemented and be provided to the devices 1510.

Also, since the server 1500 manages users and the user devices 1510 of a local network at an upper level of the local network and controls connection and association between the local network and external networks, various convergence services provided by different service providers may be individually or integrally provided to the user devices 1510.

As described above, information regarding user's personal medicines may be integrated, and thus, identification information and personal medication information, such as a medicine-taking history regarding the user's personal medicines, may be managed.

Furthermore, even a user medicine of which a name is not accurately known may be identified by performing recognition training of the user medicine based on appearance of the user medicine, and thus personal medication information, such as a medicine-taking history and a prescription history, may be provided to a user. Non-prescription medicine product information provided by pharmaceutical companies, e.g., effects and ingredients of user's personal medicines, may also be provided.

Accordingly, a user may timely take an accurate dose of medicine, may be protected from drug abuse, and may efficiently keep medicines by selectively disusing unnecessary medicines.

The exemplary embodiments may be written as computer programs and may be implemented in general-use digital computers that execute the programs using a computer readable recording medium. Examples of the computer readable recording medium include magnetic storage media (e.g., ROM, floppy disks, hard disks, etc.), optical recording media (e.g., CD-ROMs, or DVDs), etc.

While the exemplary embodiments have been particularly shown and described, it will be understood by one of ordinary skill in the art that various changes in form and details may be made therein without departing from the spirit and scope of the invention as defined by the following claims. The exemplary embodiments should be considered in a descriptive sense only and not for purposes of limitation. Therefore, the scope of the invention is defined not by the detailed description of the invention but by the following claims, and all differences within the scope will be construed as being included in the present invention.

What is claimed is:

1. A method of providing a personal medicine information management service by a user device that communicates with a server, the method comprising:
   photographing a user medicine of a user to obtain a medicine image of the user medicine;
   transmitting to the server a request for recognition of the user medicine, the request comprising the obtained medicine image; and
   receiving medicine quantity information of the user medicine and personal medicine information of the user from the server, based on a result of the recognition of the user medicine,
   wherein the personal medicine information comprises an image of the user medicine of which recognition is performed by the server, and
   wherein the result of the recognition of the user medicine is based on identification information, and the identification information is obtained from appearance of the user medicine by the server.

2. The method of claim 1, wherein a medicine-taking history from among pieces of the personal medicine information is updated based on the medicine quantity information read by the server from the medicine image.

3. The method of claim 1, wherein the receiving of the personal medicine information comprises receiving at least one of a prescription history, a purchase history, a medicine-taking history, and a disease history of the user regarding the user medicine from among pieces of the personal medicine information stored in the server.

4. The method of claim 1, wherein the receiving of the personal medicine information comprises receiving at least one of non-prescription medicine identification information and non-prescription medicine product information regarding the user medicine from among pieces of non-prescription medicine information stored in the server.

5. The method of claim 1, wherein the personal medicine information comprises information regarding at least one user medicine.

6. The method of claim 1, wherein the receiving of the personal medicine information comprises receiving a recognition failure message from the server if it is determined that the user medicine is not a personal medicine, based on the result of the recognizing.

7. The method of claim 1, wherein the server comprises a cloud computing based virtual server.

8. A method of providing a personal medicine information management service by a server, the method comprising:
   receiving from a user device a request to recognize of a user medicine of a user, the request comprising a medicine image of the user medicine;
   analyzing the received medicine image to recognize the user medicine and to determine a remaining quantity of the user medicine; and
   transmitting to the user device medicine quantity information of the remaining quantity of the user medicine and personal medicine information of the user stored in the server, based on a result of the analyzing,
   wherein the personal medicine information comprises an image of the user medicine of which recognition is performed by the server, and
   wherein the analyzing the received medicine image comprises obtaining identification for anon, and the identification information is obtained from appearance of the user medicine.

9. The method of claim 8, further comprising updating a medicine-taking history from among pieces of the personal medicine information based on the medicine quantity information read from the medicine image.

10. The method of claim 8, wherein the transmitting of the personal medicine information comprises transmitting at least one of a prescription history, a purchase history, a medicine-taking history, and a disease history of a user regarding the user medicine from among pieces of the personal medicine information stored in the server.

11. The method of claim 8, wherein the transmitting of the personal medicine information comprises transmitting at least one of non-prescription medicine identification information and non-prescription medicine product information regarding the user medicine from among pieces of non-prescription medicine information stored in the server.

12. The method of claim 8, wherein the personal medicine information comprises information regarding at least one user medicine.

13. The method of claim 8, wherein the transmitting of the personal medicine information comprises transmitting a recognition failure message to the user device if it is determined that the user medicine is not a personal medicine, based on the result of the analyzing.

14. The method of claim 8, wherein the server is a cloud computing based virtual server.

15. A method of providing a personal medicine information management service by a server, the method comprising:
receiving from a user device a medicine image of a user medicine of a user, as a request for recognition of the user medicine; and
adding the user medicine to personal medicine information of the user based on the received medicine image; and
receiving a tag for identifying the user medicine from the user device and storing the received tag.

16. The method of claim 15, further comprising transmitting to the user device a training completion message informing that the recognition of the user medicine is completed.

17. The method of claim 15, wherein the receiving of the medicine image comprises repeatedly receiving a plurality of different medicine images captured by photographing the user medicine until the recognition training of the user medicine is completed.

18. The method of claim 15, wherein the receiving of the medicine image comprises:
checking whether the received medicine image is included in the personal medicine information stored in the server; and
performing the recognition training by using the received medicine image if the received medicine image is not included in the personal medicine information.

19. The method of claim 15, the medicine image comprises at least one of an image showing a shape of a medicine, and an image showing a shape of a medicine package.

20. The method of claim 15, wherein the medicine image comprises at least one of an image showing non-prescription medicine identification information of the user medicine, and an image showing non-prescription medicine product information of the user medicine, which are readable from the appearance of the user medicine.

21. The method of claim 15, wherein the personal medicine information comprises at least one of a prescription history, a purchase history, a medicine-taking history, and a disease history of the user regarding the user medicine.

22. The method of claim 15, wherein the personal medicine information comprises information regarding at least one user medicine.

23. The method of claim 15, wherein the server comprises a cloud computing based virtual server.

24. A user device for providing a personal medicine information management service, the user device comprising:
a medicine image obtaining unit that obtains a medicine image of a user medicine of a user;
a medicine recognition requesting unit that transmits to a server a request for recognition of the user medicine, the request comprising the obtained medicine image; and
a medicine information receiving unit that receives medicine quantity information of the user medicine and personal medicine information of the user from the server based on a result of the recognition of the user medicine,
wherein the personal medicine information comprises an image of the user medicine of which recognition is performed by the server, and
wherein the result of the recognition of the user medicine is based on identification information, and the identification information is obtained from appearance of the user medicine by the server.

25. A server for providing a personal medicine information management service, the server comprising:
a medicine information storage that stores personal medicine information of a user;
a medicine recognition request receiving unit that receives from a user device a request for recognition of a user medicine of the user, the request comprising a medicine image of the user medicine;
a medicine image reading unit that analyzes the received medicine image to recognize the user medicine and to determine a remaining quantity of the user medicine; and
a medicine information transmitting unit that transmits to the user device medicine quantity information of the remaining quantity of the user medicine and the personal medicine information stored in the server, based on a result of the analyzing,
wherein the personal medicine information comprises an image of the user medicine of which recognition is performed by the server, and
wherein the analyzing the received medicine image comprises obtaining identification information, and the identification information is obtained from appearance of the user medicine.

26. The server of claim 25, further comprising a personal medicine information processing unit that sets the personal medicine information,
wherein the medicine information storage updates a medicine-taking history from among pieces of the personal medicine information based on the medicine quantity information read from the medicine image.

27. A server for providing a personal medicine information management service, the server comprising:
a medicine information storage that stores personal medicine information of a user;
a medicine recognition training request receiving unit that receives from a user device a request for recognition of a user medicine of the user, the request comprising a medicine image of the user medicine; and
a personal medicine information processing unit that adds the user medicine into the personal medicine information based on recognition of the received medicine image,
wherein the server receives a tag for identifying the user medicine from the user device and stores the received tag.

28. A non-transitory computer-readable recording medium having recorded thereon a computer program for executing the method of claim 1.

29. A non-transitory computer-readable recording medium having recorded thereon a computer program for executing the method of claim 8.

30. A non-transitory computer-readable recording medium having recorded thereon a computer program for executing the method of claim 15.

* * * * *